United States Patent [19]

Privitera

[11] Patent Number: 4,826,760

[45] Date of Patent: May 2, 1989

[54] METHOD FOR DETERMINING HELPER/SUPPRESSOR CELL RATIO IN BLOOD

[76] Inventor: James R. Privitera, 105 N. Grandview Ave., Covina, Calif. 91723

[21] Appl. No.: 922,243

[22] Filed: Oct. 23, 1986

[51] Int. Cl.$^4$ ............... G01N 33/546; G01N 33/547; G01N 33/577

[52] U.S. Cl. ............................ 435/7; 435/29; 435/39; 436/177; 436/533; 436/534; 436/548

[58] Field of Search ............... 435/2, 7, 29, 39; 436/63, 533, 534, 177, 548

[56] References Cited

U.S. PATENT DOCUMENTS 4,677,061  6/1987  Rose et al. ........................ 424/7.1

OTHER PUBLICATIONS

Chi et al., *Journal Immunol. Meth*, 19, 169–172, 1979.

*Primary Examiner*—Sam Rosen
*Assistant Examiner*—David A. Saunders
*Attorney, Agent, or Firm*—Edgar W. Averill, Jr.

[57] ABSTRACT

An improved method for determining a helper/suppressor ratio of lysed whole blood. The process includes the steps of high speed microcentrifuging the lysed whole blood, decanting, washing and resuspending the sample followed by a second high speed microcentrifuging step. The supernatant fluid is poured off and a tagging solution containing colored beads which bind to T4 and T8 lymphocytes is added followed by low speed microcentrifuging, incubating and counting under a microscope.

3 Claims, No Drawings

METHOD FOR DETERMINING HELPER/SUPPRESSOR CELL RATIO IN BLOOD

BACKGROUND OF THE INVENTION

The field of the invention is laboratory procedures and the invention relates more particularly to a procedure for determining the T4/T8 cell ratio which is often referred to as the "helper/suppressor" ratio.

In the past, a lengthy procedure was used requiring in excess of two hours to perform. More specifically, the prior art procedure started by transferring a 250 microliter sample of anticoagulant-treated blood into a centrifuge tube where 2 milliliters of a lysing reagent were added. The lysed blood mixture was incubated for five minutes and a cell wash solution was then added to the resulting lysed sample. The sample was then centrifuged for three minutes at 150×G. The supernatant fluid was then decanted and a new 8 milliliter portion of wash solution was added and the fluid was mixed and once again centrifuged for three minutes at 150×G. After a second decanting step, the pellet was suspended in 10 milliliters of wash solution and 200 microliters of colored bead solution was added. The fluid was then centrifuged again for three minutes at 150×g and incubated at ten minutes at room temperature. The supernatant fluid was then decanted and the pellet was resuspended and transferred to a microscope slide.

SUMMARY OF THE INVENTION

It is, thus, an object of the present invention to provide a rapid method for determining T4/T8 cell ratios.

The present invention is for an improved method of determining a helper/suppressor ratio in lysed whole blood of the type including the steps of drawing a sample of whole blood, incubating the sample with a lysing reagent leaving behind intact white blood cells, centrifuging, decanting, resuspending and adding colored beads to the resuspended suspension. The improvement of the present invention comprises high speed microcentrifuging the lysed whole blood for about fifteen seconds after the incubating step. Next, the supernatant fluid is poured off and resuspended in a wash solution and the resuspended fluid is again microcentrifuged. The supernatant fluid is discarded and the solids are resuspended in a tagging solution, which suspension is subjected to low speed microcentrifuging. The centrifuged, tagged fluid is incubated, resuspended and counted on a microscope slide.

DESCRIPTION OF THE PREFERRED EMBODIMENTS

The process of the present invention utilizes several microcentrifuging steps which greatly facilitate the carrying out of the procedure. A preferred series of steps includes the following:

A sample of blood is drawn using a tube with an anticoagulant such as EDTA. One to two milliliters of blood is sufficient which is maintained at room temperature. Seventy microliters of the blood is put in the bottom of a 1.9 milliliter centrifuge tube and a lymphocyte concentrate reagent is added to the fill line of the 1.9 milliliter centrifuge tube. The lymphocyte concentrate reagent contains 0.826 grams of ammonium chloride, 0.1 grams of potassium bicarbonate and 3.7 milligrams of EDTA (tetrasodium salt). After adding the lymphocyte concentrate reagent, the fluid is mixed by inverting the tube several times for five minutes until hemolysis is evident as the fluid becomes more clear. The fluid is then microcentrifuged for fifteen seconds at high speed. High speed refers to a centrifugal force of 13,000G. The supernatant fluid is then poured off and the pellet is resuspended in a cell wash solution comprising a 5× concentrate of Dulbecco's phosphate buffered saline. The resuspended pellet is then microcentrifuged for fifteen seconds at high speed. Once again, the supernatant is poured off and fifty microliters of a tagging solution sold under the trademark "IMMUTAGS Solution No. 3.". This solution contains colored beads in two colors. A group of yellow beads tends to bind to T8 cells and under a microscope, the cell appears as a rosette having at least three yellow tags attached to it. Similarly, T4 (helper) cells, have three or more red tags attached to them as viewed under a microscope. After adding the Immutags solution, the pellet is again resuspended and microcentrifuged, this time in a low speed for fifteen seconds. A low speed is equivalent to a centrifugal force of 1000G. The centrifuged pellet and solution are allowed to stand for about five minutes at room temperature in a vertical position, after which they are resuspended by gentle rotation. About five microliters of cell suspension are placed on a slide and the suspension is covered with a cover slip and the rosettes are counted. After 100 rosettes are counted, the ratio of T4 (helper) cells, which are red, is divided by the number of T8 (suppressor) cells, which appear as yellow rosettes.

It has been known that human T lymphocytes may be classified into subpopulations on the basis of function and/or the presence of unique antigenic determinants. Monoclonal antibodies have been developed against these antigens and provide a means of identifying these cells using standard immunological methods. The two T lymphocyte subsets of clinical interest are regulatory T cells. Helper/inducer T cells are those cells which bear the T4 membrane antigen.. This subset comprises approximately 65% of peripheral blood lymphocytes in normal individuals. Supressor/cytotoxic T cells bear the T8 antigen. These cells represent approximately 35% of peripheral blood lymphocytes. In vitro studies indicate that the T4 subset provides help for B cell immunoglobulin production, while the T8 subset suppresses immunoglobulin production by B cells in the presence of T4 helper cells. Analyzing T cells subsets has proved to be valuable for renal transplant patients and T cell subset studies may prove useful in allergy, viral infection, cancer and aging.

It is, thus, believed that the determination of the balance between T4 and T8 lymphocyte subsets can provide insight into many diseases and disorders. By providing a simpler and faster method of determining this ratio, this test can be readily performed by the office practitioner to assist in diagnosing and treating a wide range of disorders.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. An improved method of determining a helper/suppressor ratio in lysed whole blood including the steps of drawing a sample of whole blood, incubating the sample with a lysing reagent leaving behind intact white blood cells, centrifuging, decanting, resuspending and adding colored beads to the resuspended suspension wherein the improvement comprises:

high speed microcentrifuging at an acceleration of about 13,000 ×G, the lysed whole blood for about fifteen seconds after the incubating step;

decanting the supernatant fluid and resuspending the pellet in a wash solution to produce a first resuspended fluid and high speed microcentrifuging at the first resuspended fluid at an acceleration of about 13,000×G;

decanting the supernatant wash fluid and resuspending the pellet in an immunologic tagging solution containing colored beads which include beads of a first color which selectively bind to T4 lymphocytes and beads of a second color which selectively bind to T8 lymphocytes to produce a resuspended tagged suspension;

low speed microcentrifuging, at an acceleration of about 1000×G, the resuspended tagged suspension to produce a centrifuged tagged fluid;

incubating the centrifuged tagged fluid to produce an incubated, tagged fluid including rosettes of a first color and rossettes of a second color;

resuspending the incubated, tagged fluid with gentle rotation to produce a tagged suspension; and placing a sample of the tagged suspension on a slide and covering with a cover slip and counting the rosettes of the first color and the rosettes of the second color whereby the helper/suppressor ratio may be ascertained by dividing the number of rosettes of the first color by the number of rosettes of the second color.

2. The process of claim 1 wherein the incubating of the centrifuged tagged fluid step is for a period of about five minutes.

3. The process of claim 1 wherein the high speed microcentrifuging steps are for a period of about fifteen seconds.

* * * * *